United States Patent [19]

Kinnunen et al.

[11] Patent Number: 5,792,612
[45] Date of Patent: Aug. 11, 1998

[54] USE OF LIPIDS TO IMPROVE THE POLYMERSE CHAIN REACTION

[75] Inventors: Paavo Kai Johannes Kinnunen; Pekka Kristian Mustonen, both of Espoo; Juha Kalervo Kere, Helsinki, all of Finland

[73] Assignee: Helsinki University Licensing, Ltd., Helsinki, Finland

[21] Appl. No.: 493,108

[22] Filed: Jun. 20, 1995

Related U.S. Application Data

[63] Continuation-in-part of Ser. No. 264,080, Jun. 22, 1994, abandoned.
[51] Int. Cl.$^6$ ............... C12Q 1/68; C12P 19/37; C07H 21/00; G01N 33/92
[52] U.S. Cl. ............ 435/6; 435/91.2; 435/91.1; 536/25.3; 436/71
[58] Field of Search ............... 435/91.2, 91.1, 435/6; 536/25.3; 436/71

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 5,585,112 | 12/1996 | Unger | 424/450 |

FOREIGN PATENT DOCUMENTS

| | | | |
|---|---|---|---|
| 0 555 797 A1 | 8/1993 | European Pat. Off. | C12N 9/22 |
| 40 00 247 A1 | 7/1991 | Germany | C12P 1/00 |
| WO 93/16200 | 8/1993 | WIPO | C12Q 1/68 |

OTHER PUBLICATIONS

Batzri & Korn, "Single Bilayer Liposomes Prepared without Sonication," *Biochem. Biophys. Acta*, 298:1015–1019 (1973).

Boehringer Mannheim Biochemica Katalog, "Inkubationspuffer–Set für Restrictionsenzyme," p. 444 (1991).

Bryant & Christie, "Induction of Chromosomal Aberrations in CHO Cells by Restriction Endonucleases: Effects of Blunt– and Cohesive–Ended Double–Strand Breaks in Cells Treated by 'Pellet' Methods," *Mutation Research*, 213:233–241 (1989).

Budker et al., "Cleavage of DNA Adsorbed on Model Phospholipid Membranes by Restriction Endonucleases," *Chemical Abstracts*, 106(19):152013 (May 11, 1987), (Abstract 106:152013B).

Saiki, R.K., "The Design and Optimization of the PCR," *In: PCR Technology: Principles and Applications for DNA Amplification*, Erlich, H. A., (Ed.), M Stockton Press, New York, US, Chapter 1, pp. 7–22 (1989).

Harrison & Zimmerman, "Polymer–Stimulated Ligation: Enhanced Ligation of Oligo– and Polynucleotides by T4 RNA Ligase in Polymer Solutions," *Nucleic Acids Res.*, 12(21):8235–8251 (Nov. 12, 1984).

Hayashi et al., "Influence of Monovalent Cations on the Activity of T4 DNA Ligase in the Presence of Polyethylene Glycol," *Nucleic Acids Res.*, 13(9):3261–3271 (May 10, 1985).

Hayashi et al., "Regulation of Inter– and Intramolecular Ligation with T4 DNA Ligase in the Presence of Polyethylene Glycol," *Nucleic Acid Res.*, 14(19):7617–7631 (Oct. 10, 1986).

Hayashi et al., "Stimulations of Intermolecular Ligation with *E. coli* DNA Ligase by High Concentrations of Monovalent Cations in Polyethylene Glycol Solutions," *Nucleic Acids Res.*, 13(22):7979–7992 (Nov. 25,1985).

Heitman & Model, "SOS Induction as an in Vivo Assay of Enzyme–DMA Interactions," *Gene*, 103(1):1–9 (1991).

Heitman, J., "On the Origins, Structures and Functions of Restriction–Modification Enzymes," *Genetic Engineering, Principles and Methods*, 15:57–108 (1993).

Innis & Gelfand, "Optimization of PCRs," *In: PCR Protocols: A Guide to Methods and Applications*, Innis et al., (Eds.), Academic Press, Inc., Harcourt Brace Jovanovich, Publishers, New York, US, pp. 3–12 (1990).

Kere et al., "Mapping Human Chromosomes by Walking with Sequence–Tagged Sites from End Fragments of Yeast Artificial Chromosomes Inserts," *Genomics*, 14:241–248 (1992).

Keren–Zur et al., "Induction of Fusion in Aggregated and Nonaggregated Liposomes Bearing Cationic Detergents," *Biochimica et Biophysica Acta*, 983(2):253–258 (1989).

Kunkel et al., "The Fidelity of DNA Polymerases Used in the Polymerase Chain Reaction," *In: PCR: A Practical Approach*, McPherson et al., (Eds.), The Practical Approach Series, Series Editors, Rickwood, D. & Hames B.D., pp. 225–243 (1991).

Lavery & Kowalczykowski, "Enhancement of recA Protein–Promoted DNA Strand Exchange Activity by Volume–Occupying Agents," *J. Biol. Chem.*, 267(13):9307–9314 (May 5, 1992).

McClelland et al., "KGB: A Single Buffer For All Restriction Endonucleases," *Nucleic Acids Research*, 16(1):364 (Jan. 11, 1988).

Mixich, F., "Induction of Chromosomal Aberrations by Restriction Endonucleases Encapsulated in Liposomes," *Mutation Research*, 262:177–181 (1991).

New England BioLabs 1995 Catalog, "NEBuffer Activity Chart for Restriction Endonucleases," pp. 196–197 (1995).

Newton & Graham, (Eds.), "Geräte, Reagentien und Hilfsmittel," *In: PCR*, Spektrum Akademischer Verlag Heidelberg, Berlin, Oxford, pp. 27–46 (1994).

Obe et al., "Chromosomal Abberations Induced by Restriction Endonucleases," *Mutation Research*, 150:359–368 (1985).

(List continued on next page.)

*Primary Examiner*—Kenneth R. Horlick
*Assistant Examiner*—Joyce Tung
*Attorney, Agent, or Firm*—Marshall, O'Toole, Gerstein, Murray & Borun

[57] ABSTRACT

Disclosed are improvements for enzyme-catalyzed reactions involving DNA or RNA, including PCR, which are based on conducting such reactions in the presence of lipids.

36 Claims, 3 Drawing Sheets

OTHER PUBLICATIONS

Takahashi & Uchida, "Thermophilic HB8 Ligase: Effects of Polyethylene Glycol and Polyamines on Blunt–End Ligation of DNA," *J. Biochem.*, 100(1):123–131 (Jul., 1986).

Teraoka & Tsukada, "Influence of Polyethylene Glycol on the Ligation Reaction with Calf Thymus DNA Ligases I and II," *J. Biochem.*, 101(1):225–231 (Jan. 1987).

Kere, et al., "Mapping Human Chromosomes by Walking with Sequence–Tagged Sites from End Fragments of Yeast Artificial Chromosome Inserts," *Genomics*, 14:241–248 (1992).

Budker, et al., *Chemical Abstracts*, 116:152013b (1987).

Mixich, "Induction of chromesomal aberrations by restriction endonucleases encapsulated in liposomes," *Mutation Research*, 262:177–181 (1991).

Bryant, et al., "Induction of chromosomal aberrations in CHO cells by restriction endonucleases: effects of blunt- and cohesive–ended double–strand breaks in cells treated by 'pellet' methods," *Mutation Research*, 213:233–241 (1989).

Obe, et al., "Chromosomal aberrations induced by restriction endonucleases," *Mutation Research*, 150:359–368 (1985).

Oberhlzer et al. Polymerase chain reaction in liposomes, Chem. Biol. vol. 2(10), pp. 677–682, 1995.

Koiv et al. Evidence for Ternary Complex Formation by Histone H1, DNA, and Liposomes, Biochemistry, vol. 43, pp. 8018–8027, 1995.

USE OF LIPIDS TO IMPROVE THE POLYMERSE CHAIN REACTION

This is a continuation-in-part of U.S. patent application Ser. No. 08/264,080, filed Jun. 22, 1994 now abandoned.

FIELD OF THE INVENTION

The present invention generally relates to materials and methods for the controlled modification of DNA- or RNA-enzyme interactions by coupling such reactions to lipids.

BACKGROUND OF THE INVENTION

Enzymes which act upon DNA or RNA, such as restriction endonucleases and exonucleases, ligases, polymerases, and others, have become widely available for use in research applications requiring modification, copying, and/or activation (e.g., transcription) of DNA. For example, the development of thermostable polymerases for use in the polymerase chain reaction (hereinafter referred to as "PCR") has greatly facilitated the use of that technique in the amplification of portions of even the most complex genomes.

Of interest to the present invention are numerous methods involving DNA or RNA modification which are improved upon by the invention. In the present invention, methods for DNA or RNA modification include any method in which an enzyme, together with possible auxiliary proteins, acts upon DNA or RNA. For the purpose of providing background to the present invention, a representative example of a method involving DNA modification is presented below.

One of the most successful methods involving the modification of DNA is the PCR. Most commonly, PCR is used for the selective amplification of a discrete region of DNA from a larger DNA template, such as the genome of an organism, or a portion thereof. The PCR technique utilizes the ability of small segments of DNA (primers) to anneal to portions of a larger single-stranded DNA template which are complementary to the primer sequence. A DNA polymerase is then used to extend the primer in the 5' to 3' direction along the template. The result is a DNA strand extended from the primer which is complementary to the template. Two primers are normally employed, one of which binds to a portion of one of the complementary strands of a double-stranded DNA template, and the other of which binds to a portion of the opposite complementary strand of the same template, such that the 3' ends of the primers point toward each other. The two primers are positioned such that extension of each primer generates a new template for the opposite primer (i.e., the primer which bound to the opposite strand of the original template).

The reaction begins when a piece of DNA which contains the sequence of interest (the template) is denatured (by heating, usually to 94° C.) in the presence of a large molar excess of specific primers as described above. Renaturation (by cooling, usually at 37°–72° C.) results in binding of the primers to the template. A thermostable DNA polymerase and a mixture of the four common nucleotides are also present. Polymerization, resulting in primer extension, is then allowed to occur at the optimal temperature for the polymerase (72° C. for the most common polymerase, the taq polymerase). Cycles of denaturation, renaturation, and polymerization are then continuously repeated, eventually resulting in a doubling, in each cycle, of the amount of a product roughly equivalent in length and sequence to the discrete region of DNA sought to be amplified. Obviously, the eventual doubling of the product with each cycle results in the production of large amounts of the discrete sequence to be amplified.

The applications of PCR in molecular biology are legion and will not be addressed here. However, it is of interest to the present invention that standard PCR protocols require that the denaturation, renaturation, and polymerization cycles occur at specific temperatures. Those temperatures are primarily determined by the physical chemical properties of the DNA and the polymerase used in the reaction. For example, 94° C. is usually used in the denaturing cycle because that is an optimal temperature at which DNA melting occurs. Similarly, renaturation is usually performed at a temperature which allows maximum specific template binding (most commonly 37° C). In addition, DNA polymerases generally have a temperature optimum. If the reaction is carried out at other than optimum temperature, yields are poor. However, even under optimal conditions, PCR may not produce expected yields due to inefficient extension and/or polymerization and the components, especially the polymerase, are expensive. Standard PCR protocols are generally known to those skilled in the art.

Reactions involving DNA modification, such as those described above, are conventionally carried out in aqueous solution in the presence of organic and inorganic salts, buffers, and the required enzymes. The reaction mixtures must be incubated at optimized temperatures for set periods of time in order for the reaction to run to completion. In the case of PCR, it is additionally required that repeated cycling at specific temperatures, as outlined above, be performed.

Also of interest to the present invention are lipids and their physical chemical properties. Lipids exhibit characteristic phase behavior which is a function of, inter alia, temperature and ionic concentrations. Lipid phase transitions are accompanied by dramatic alterations in physical organization. It is now firmly established that several proteins bind to lipids in biological membranes and that such binding is a function of the phase state of the membrane lipids. By changing the physical state of the lipids in the bilayer, one may cooperatively regulate the binding, and therefore, the function of proteins which bind to the lipids. Specifically, several DNA-binding proteins have been shown to bind to lipids, with resulting changes in function depending upon the lipid phase state. However, there are no reports describing the effects of lipids on restriction enzymes, polymerases, ligases, or other DNA (or RNA) processing enzymes.

Phospholipids, for example, which are found in all cellular membranes, comprise two very different physical environments, a hydrophobic interior region and a more-complex hydrophilic exterior region. The hydrophobic tails of most phospholipids exist in two fundamental physical states. At higher temperatures the hydrophobic tails are in a fluid state and generally have rotational freedom; while at lower temperatures, phospholipids are more geometrically constrained. Overall, membrane lipids may exist in varying states of order, or phases, which normally depend upon both temperature and the lipid composition. There are four major forms of organization of lipids in a biological environment (i.e., in the presence of water). The lamellar liquid crystalline phase ($L_\alpha$) is the fluid state normally depicted in representations of biological membranes. The lamellar gel phase ($L_\beta$) is formed at low temperatures in lipids in which the lamellar structure is possible. The $L_\beta$ phase is characterized by tight packing and acyl chains which are more highly ordered as compared to the $L_\alpha$ phase. The $L_\beta$ phase is also characterized by a predominance of the all-trans acyl chain configuration, resulting in greater bilayer thickness than in the $L_\alpha$ phase. In the Hexagonal I phase ($H_I$), lipids are organized in cylinder-like configurations, with the polar head groups facing outward. Finally, the Hexagonal II phase ($H_{II}$) is characterized by a hexagonal array of cylinders, but with the polar head groups facing inward, surrounding a column of water (i.e., an inverted micelle). The phase adopted by a particular lipid is a function of, inter alia, temperature and the precise mix of lipids present. For example, some lipids, such as unsaturated phospatidylethanolamines, resist bilayer formation and tend toward the $H_{II}$, configuration. However, the overall configuration of a biological membrane is determined by the sum of phospholipids present, taking into account other factors, such as temperature, ionic strength, and hydration. The kinetic properties of membranes are due, in large part, to the properties of the phospholipids which comprise them. Membrane lipids create a fluid environment in which conformational changes in both membrane proteins and the lipids themselves allow a diversity of reactions to take place at the membrane which cause changes in cellular processes, including growth. The extent of fluidity in the membrane is a function of temperature, as indicated above, and also of the ratio of phospholipid to cholesterol and the extent of saturation of membrane lipids. One of the more important roles of membrane phospholipids occurs in the regulation of binding between membrane-bound receptors and their ligands.

The present inventors have determined that DNA binds to sphingosine-containing membranes. In further studies, the inventors have determined that the presence of either pure lipids or lipid mixtures affects reaction speed, yield, specificity, and enzymatic activity with respect to RNA- and DNA-modifying enzymes, including, but not limited to nucleases, ligases, and polymerases. Thus, the present invention, based upon conducting RNA- and/or DNA-modification reactions in the presence of a lipid matrix provides means for conducting reactions involving RNA or DNA, such as PCR and restriction digests, in a manner which is faster, less expensive, and which provides higher yields as compared to conventional techniques of the art.

SUMMARY OF THE INVENTION

The present invention relates to methods and materials for enhancement of reactions involving RNA or DNA modification by conducting such reactions in the presence of lipids. Methods according to the invention result in increased reaction rates, increased yield, and decreased need for reaction components, such as enzyme.

In a preferred embodiment of the invention, a DNA is amplified by an improvement in a standard PCR method, the improvement comprising conducting the PCR in the presence of lipids. The improved method of the invention results in increased speed of the reaction, improved yields, reduced cost due to the fact that less enzyme must be used, and increased reaction specificity and fidelity in copying.

Preferred lipids for use in the present invention comprise a phosphorylcholine moiety attached to a hydrophobic tail. Highly preferred embodiments of the invention include the use of lipids such as didecylphosphatidylcholine, egg yolk phosphatidylcholine, and 1-palmytoyl-2-acetyl phosphatidylcholine in a concentration range from about 10 µM to about 50 µM.

The present invention is also useful in the improvement of the kinetics, specificity, and yield of enzyme-catalyzed reactions. Thus, in a preferred embodiment of the invention, enzymatic reactions catalyzed by nucleotide kinases and/or phosphatases are improved by conducting such reactions in the presence of a lipid suspension or matrix. Materials and methods of the invention also enable PCR to be conducted at lower temperatures than are reported in the art and such methods do not require the use of a thermostable polymerase.

Upon consideration of the present invention, the skilled artisan understands that the invention may be applied to any method in which RNA or DNA is acted upon by enzymes. Based upon the principles of the invention, it is understood that conducting such reactions in the presence of a lipid suspension or matrix increases the speed and specificity of such reactions and reduces the requirements for enzyme and other materials, resulting in a considerable cost savings. Accordingly, numerous applications of the invention, in addition to those exemplified herein, are readily apparent to the skilled artisan upon consideration of the present application.

DETAILED DESCRIPTION OF THE INVENTION

Figure 1:
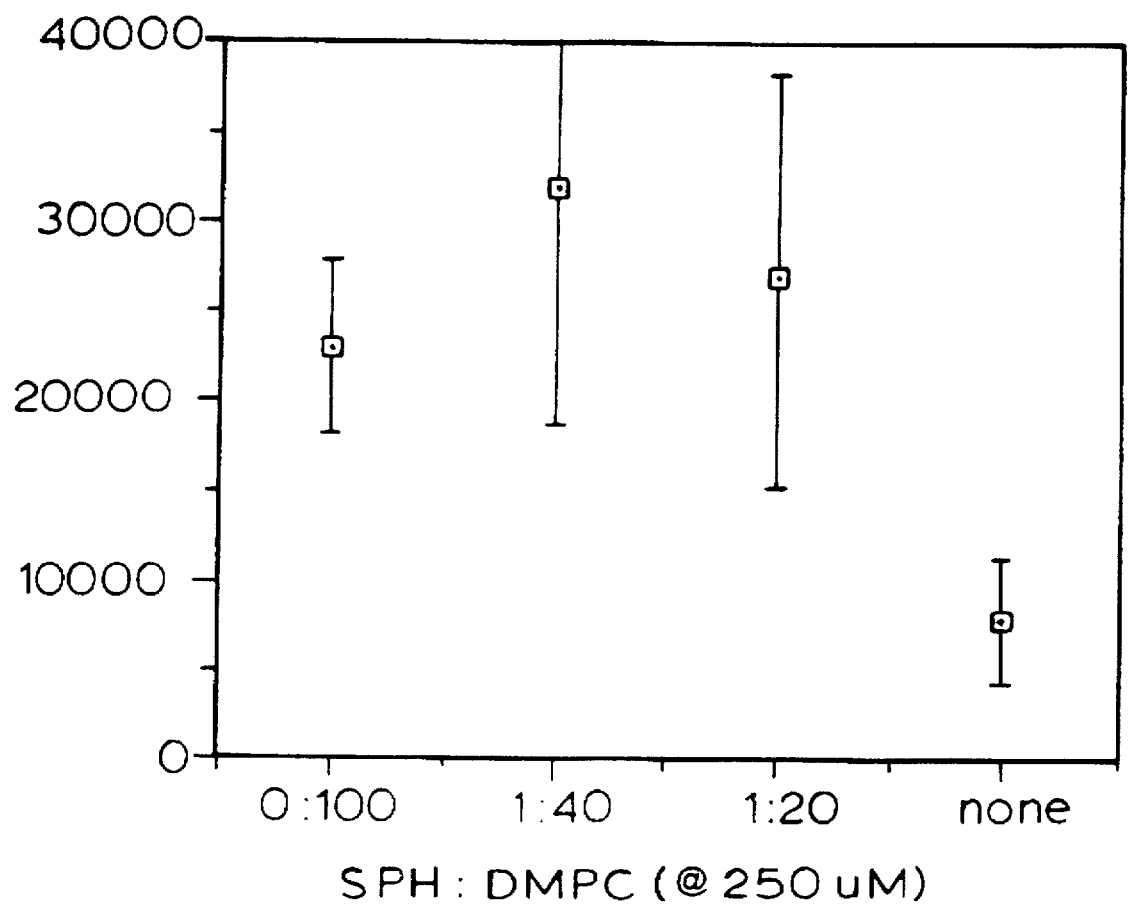
FIG. 1 shows results of a product extension assay using PCR in the presence of lipids.

Standard reaction conditions in various enzyme-catalyzed reactions, and especially such reactions involving DNA, are generally suboptimal, resulting in poor yields and reduced specificity. For example, PCR techniques result in errors in the fidelity of amplification, the magnitude of which depends upon the polymerase used and the ionic environment in which the reaction is conducted. See, e.g., Kunkel, et al., "The Fidelity of DNA Polymerase and the Polymerases used in the PCR" in *Polymerase Chain Reaction I: A Practical Approach* (McPherson, et al., eds, 1991). In addition, conventional DNA manipulation techniques are expensive due to the high cost of enzyme, especially DNA polymerases and restriction endonucleases. The present invention overcomes these and other difficulties in the art and provides a technique for greatly improving the speed, efficiency, and fidelity of methods involving the manipulation of DNA, including reductions in cost due to a reduced necessity for starting materials.

In a general sense, the present invention improves conventional techniques by tying reactions involved in those techniques to lipids. For purposes of the present invention, a lipid suspension or matrix simply means that reactions are conducted in the presence of lipid, i.e., wherein lipid is added to the reaction volume. Such improvements may be mediated through lipid-protein or lipid-DNA interactions, possibly reducing activation energies; altered dimensionality of the reactions; and other effects, either alone or in combination. Whatever the mechanism, conducting such reactions in the presence of lipids results in enhanced reaction rates, shorter incubation times, improved yields, and altered reaction temperatures.

Methods according to the invention have been successfully carried out using numerous lipids, including didecyl phosphatidylcholine, egg yolk phosphatidylcholine, dimyristoyl phosphatidylcholine, sphingomyelin, sphingosyl phosphatidylcholine, and 1-palmitoyl-2-octyl phosphatidylcholine. Both micelle-forming lipids, such as 1-palmitoyl-2-acetyl phosphatidylcholine, and liposome-forming lipids, such as didecyl phosphatidylcholine, may be used according to the invention.

The following Example provides an embodiment of the invention. Numerous additional aspects of the invention are apparent upon consideration of the following Example.

EXAMPLE

ENHANCEMENT OF THE PCR BY LIPID COUPLING

A basic PCR technique is reported in U.S. Pat. No. 4,868,202, incorporated by reference herein. Moreover, a basic approach to PCR is briefly outlined above. Accordingly, the skilled artisan is knowledgeable in applying and using the PCR and the details will not be addressed herein except as where necessary to enable practice of the invention.

A series of experiments was conducted to measure the enhancement of PCR by conducting PCR reactions in the presence of lipids. Comparisons were made by determining the reaction yield upon reaction with or without lipids and by measuring the length of polymerase-synthesized DNA with and without lipids. Typical reactions were conducted at a volume of 20 µl, using approximately 50 µg human genomic DNA as a template. Two primers (10 pmol each), GTTAAT-AGTAATGTCCTCTCTTTC (SEQ ID NO: 1) and ACCTT-TAGTTAGATTGATGAAGCC (SEQ ID NO: 2), which correspond to the 3' and 5' ends, respectively, surrounding a unique approximately 82 bp product corresponding to the unique human sequence-tagged site, sWXD178 as reported in Kere, et al., *Genomics*, 14:241–248 (1992), incorporated by reference herein, were added to the mixture. The template and product sequences are available through the GenBank database under accession number L14983 (HSSWX178) for human chromosome X STS sWXD178. A Taq polymerase (Boehringer, 0.5 U) and 0.25 µM each of dATP, dGTP, dCTP, and dTTP were used for polymerization in 50 mM KCl, 10 mM Tris-HCl, pH 8.6, 1.5 mM $MgCl_2$ and reactions were carried out in a programmable thermocycler (MJR Research). Lipid was added prior to initiation of the reaction in final concentrations of 10, 100, or 250 µM as unilamellar liposomes prepared by extrusion through 0.1 µM polycarbonate membranes with a LiposoFast Membrane Homogenizer (Avestin, Canada), as reported in McDonald, et al., *Biochem. Biophys. Acta.*, 1061:297–303 (1991), incorporated by reference herein. Standard reactions without lipid were also run in parallel. The lipids used were selected from lipids having a net positive charge at neutral pH, including stearylamine (STA), sphingosine, dimyristoylphosphatidylcholine (DMPC), and dipalmitoylphosphatidylcholine (DPPC), alone and in various combinations. The reactions were performed with and without oil overlay with essentially identical result in each case.

Each reaction mixture (i.e., PCR components with or without lipid) was first heated at 94° C. for 150 seconds followed by thirty cycles at 94° C. for 30 seconds, 20° C. for 45 seconds, and 72° C. for 45 seconds. The yield of reaction products was determined by including radiolabled deoxycytosine triphosphate in the reaction mixture and lowering the unlabeled dCTP concentration to 0.025 µM. Reaction products were then separated by agarose gel electrophoresis (a 1.5% gel stained with ethidium bromide). Only one band corresponding to the specific product was observed for each lane. The reaction products were excised from the gel and measured in a scintillation counter.

The results of the assays for product yield are presented in FIG. 1. As shown in that Figure, the amount of PCR product was increased threefold in the presence of 250 µM DMPC and fourfold in the presence of a 250 µM mixture of sphingosine and DMPC at a 1:40 ratio. Increase in the yield of reaction product was also observed when a lipid composition comprising about 90% sphingosine or STA in DMPC was added to the reaction mixture; whereas molar ratios of 15% to 80% inhibited the reaction. The presence of lipid also increased the length of single primer extension products in each case in which lipid was used, indicating that more efficient polymerization is occurring during equivalent PCR runs. The foregoing results clearly show that proper addition of lipids in a PCR results in increased yield of product and more efficient polymerization.

Figure 2:
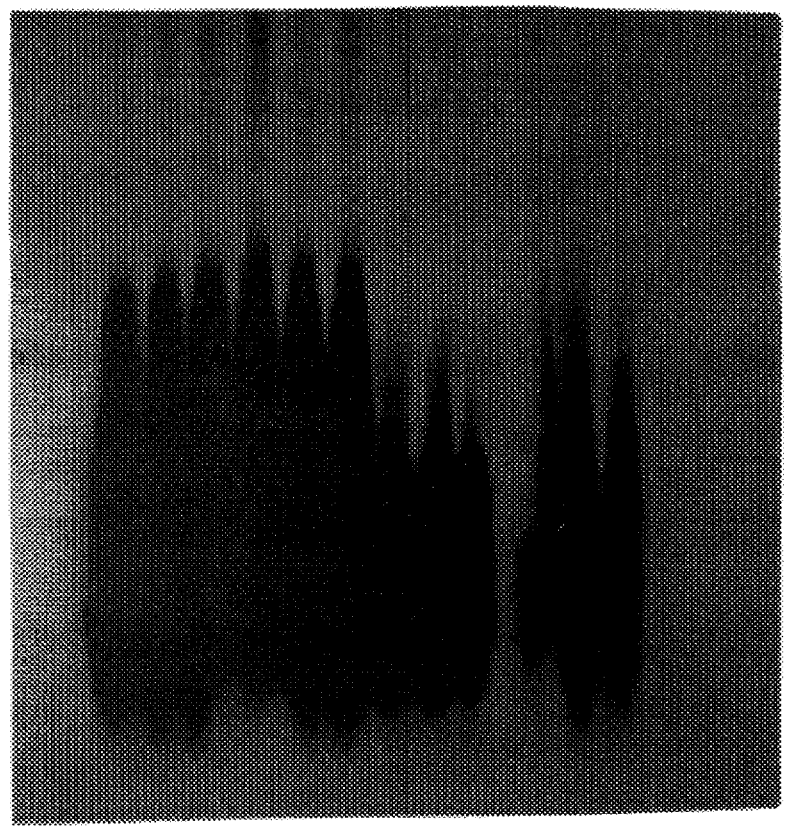
FIG. 2 shows results of a primer extension assay both with and without lipid.

Primer extension assays were performed under similar conditions. To measure the average length of extended (polymerized) products, only one primer at a time was included in the reaction in the presence of radiolabelled deoxycytosine triphosphate and unlabelled nucleotides at concentrations of 0.25 µM dATP, dGTP, and dTTP and 0.025 µM dCTP and 250 µM sphingosine:stearylamine in a 1:1 molar ratio. Identical reactions were run without lipid as controls. Reaction products obtained by primer extension were analyzed by agarose gel electrophoresis, blotted onto nylon membranes, and autoradiographed to visualize the relative molecular weights of the reaction products. As shown in FIG. 2, the length of primer extension product is increased in the presence of lipids. FIG. 2 also shows that improved yields were obtained when extension was performed in the presence of lipid. In FIG. 2, lanes 1–6 represent extension products obtained with lipid and lanes 7–12 represent extension products obtained without lipid. As shown in that Figure, primer extension products obtained from a PCR conducted in the presence of lipids have higher molecular weights and have incorporated more of the label (as indicated by intensity), indicating greater primer extension.

Figure 3:
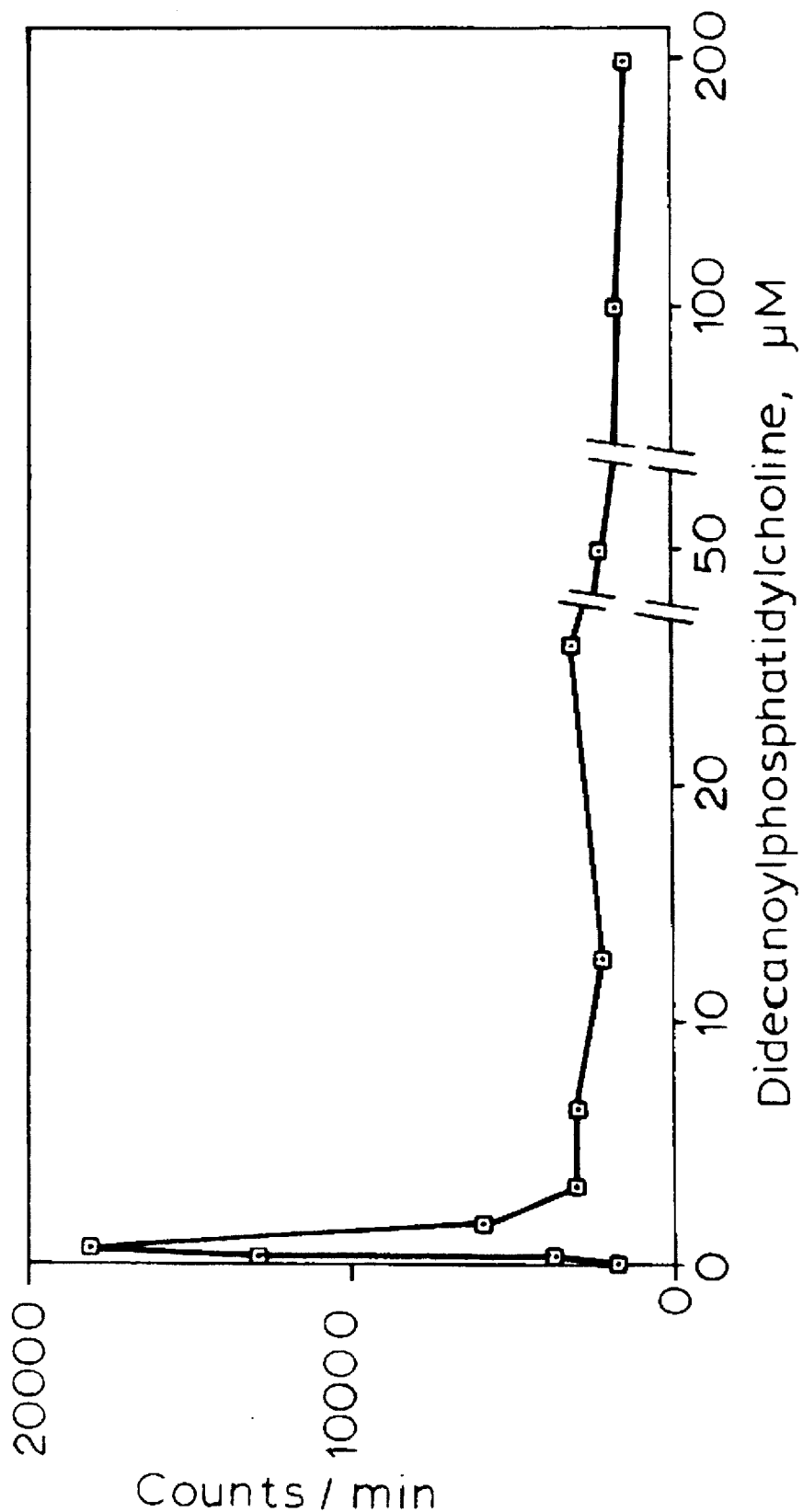
FIG. 3 shows results of PCR amplification in the presence of didecyl phosphatidylcholine.

In a separate experiment, the polymerase chain reaction was run for 30 cycles as indicated above in the presence of 0.2, 0.4, 0.8, 1.6, 3.1, 6.2, 12.5, 25, 50, 100, or 200 µM concentrations of didecylphosphatidylcholine. As shown in FIG. 3, optimal amplification was obtained using between 0.2 µM and 3.1 µM concentrations of the lipid. Three separate controls were run and results showed that PCR product isolated was about 1/10 of that isolated using between about 0.2 µM and about 3.1 µM concentrations of didecylphosphatidylcholine.

The results reported above show that the use of lipids in the PCR results in higher yields of PCR products and greater fidelity of amplification.

---

What is claimed is:

1. In a method of amplifying nucleic acids by the polymerase chain reation, comprising forming an amplification reagent mixture and subjecting said mixture to repeated cycles of denaturation, annealing, and extension, the improvement comprising adding a lipid to said amplification reagent mixture.

2. The method according to claim 1, wherein said lipid is selected from the group consisting of didecyl phosphatidylcholine, egg phosphatidylcholine, 1-palmitoyl-2-acetyl phosphatidylcholine, dimyristoyl phosphatidyicholine, and lysophosphatidylcholine.

3. The method according to claim 1, wherein said lipid is present in said amplification reagent mixture in a concentration from about 10 μM to about 50 μM.

4. In a polymerase chain reaction (PCR) method of amplifying nucleic acid, comprising the steps of providing an amplification reagent mixture and subjecting said mixture to repeated cycles of denaturation, annealing, and extension, the improvement comprising including in said amplification reagent mixture a lipid composition at a concentration effective to improve at least one of the kinetics and yield of the PCR reaction.

5. The method according to claim 4 wherein said lipid composition is added to said mixture to provide a lipid concentration effective to yield more PCR product DNA than an identical PCR method wherein said amplification reagent mixture is free of said lipid composition.

6. The method according to claim 4 wherein said lipid composition comprises a lipid having a net positive charge at neutral pH.

7. The method according to claim 4 wherein said lipid composition comprises a lipid that comprises a phosphorylcholine moiety attached to a hydrophobic tail.

8. The method according to claim 4 wherein said lipid composition comprises a phosphatidylcholine (PC).

9. The method according to claim 8 wherein said lipid composition is added to said mixture to provide a lipid concentration in said mixture of 0.2 μM to 50 μM.

10. The method according to claim 8 wherein said lipid composition is added to said mixture to provide a lipid concentration in said mixture of about 10 μM to about 50 μM.

11. The method according to claim 8 wherein said lipid composition is added to said mixture to provide a lipid concentration in said mixture of 0.2 μM to 10 μM.

12. The method according to claim 8 wherein said phosphatidylcholine (PC) is selected from the group consisting of didecyl PC, 1-palmitoyl-2-acetyl PC, dimyristoyl PC, sphingosyl PC, dipalmitoyl PC, 1-paimitoyl-2-octyl PC, and mixtures thereof.

13. The method according to claim 12 wherein said lipid composition is added to said mixture to provide a lipid concentration in said mixture of about 10 μM to about 50 μM.

14. The method according to claim 8 wherein said lipid composition comprises didecyl PC.

15. The method according to claim 14 wherein said lipid composition is added to said mixture to provide a lipid concentration in said mixture of 0.2 μM to 10 μM.

16. The method according to claim 14 wherein said lipid composition is added to said mixture to provide a lipid concentration in said mixture of 0.2 μM to 3.1 μM.

17. The method according to claim 8 wherein said lipid composition comprises 1-palmitoyl-2-acetyl PC.

18. The method according to claim 8 wherein said lipid composition comprises phosphatidylcholine derived from egg yolk.

19. The method according to claim 8 wherein said lipid composition consists essentially of phosphatidylcholine (PC).

20. The method according to claim 8 wherein said lipid composition further includes at least one of stearylamine and sphingosine at a concentration effective to increase the yield of PCR reaction product.

21. The method according to claim 20 wherein said lipid composition comprises a phospatidylcholine (PC) and at least one of stearylamine and sphingosine, and wherein the molar ratio of said PC to said sphingosine or STA is about 1:9.

22. The method according to claim 8 wherein said lipid composition comprises dimyristoyl PC and sphingosine at a molar ratio of dimyristoyl PC to sphingosine greater than or equal to 20:1.

23. The method according to claim 4 wherein said lipid composition comprises stearylamine.

24. The method according to claim 23 wherein said lipid composition further comprises sphingosine.

25. The method according to claim 4 wherein said lipid composition comprises sphingosine.

26. The method according to claim 4 wherein said lipid composition comprises sphingomyelin.

27. The method according to claim 4 wherein said lipid composition is added to said mixture to provide a lipid concentration in said mixture of 0.2 µM to 250 µM.

28. The method according to claim 4 wherein said lipid composition is added to said mixture to provide a lipid concentration in said mixture of 0.2 µM to 50 µM.

29. The method according to claim 4 wherein said lipid composition is added to said mixture to provide a lipid concentration in said mixture of about 10 µM to about 50 µM.

30. The method according to claim 4 wherein said lipid composition is added to said mixture to provide a lipid concentration in said mixture of about 0.2 µM to about 10 µM.

31. The method according to claim 4 wherein said lipid composition is added to said mixture to provide a lipid concentration in said mixture of 0.2 µM to 3.1 µM.

32. The method according to claim 4 wherein said lipid composition consists essentially of lipids having a net positive charge at a neutral pH.

33. The method according to claim 4 wherein the lipid composition consists essentially of lipids.

34. The method according to claim 4 wherein said amplification reagent mixture comprises a single primer and wherein said lipid composition is present in said mixture at a concentration whereby said PCR method yields PCR product of a greater average length than an identical PCR method wherein said mixture is free of said lipid composition.

35. A polymerase chain reaction (PCR) method for amplifying DNA, comprising the steps of:
 (a) preparing a PCR amplification reagent mixture comprising:
  (i) a template comprising isolated DNA or RNA,
  (ii) a lipid,
  (iii) a DNA polymerase,
  (iv) at least one oligonucleotide primer;
  (v) dATP, dTTP, dGTP, and dCTP, and
  (vi) a suitable PCR reaction buffer; and
 (b) subjecting said mixture to repeated cycles of denaturation, annealing, and extension.

36. A polymerase chain reaction (PCR) method for amplifying DNA, comprising the steps of:
 (a) preparing a solution comprising:
  (i) a nucleic acid template,
  (ii) a DNA polymerase,
  (iii) at least one oligonucleotide primer;
  (iv) dATP, dTTP, dGTP, and dCTP, and
  (v) a suitable PCR reaction buffer;
 (b) adding a lipid to said solution at a concentration effective to increase the kinetics or yield of a PCR reaction, thereby providing an amplification reagent mixture; and
 (c) subjecting said mixture to repeated cycles of denaturation, annealing, and extension.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

-continued ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

GTTAATAGTA ATGTCCTCTC TTTC     24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

ACCTTTAGTT AGATTGATGA AGCC     24